United States Patent [19]
Yoon

[11] Patent Number: 5,713,870
[45] Date of Patent: Feb. 3, 1998

[54] RETRACTABLE SAFETY PENETRATING INSTRUMENT WITH LATERALLY EXTENDABLE SPRING STRIP

[76] Inventor: InBae Yoon, 2101 Highland Ridge Dr., Phoenix, Md. 21131

[21] Appl. No.: 424,784

[22] Filed: Apr. 19, 1995

Related U.S. Application Data

[63] Continuation-in-part of Ser. No. 247,205, May 20, 1994, Pat. No. 5,634,934, and Ser. No. 79,586, Jun. 22, 1993, Pat. No. 5,423,770, which is a division of Ser. No. 868,578, Apr. 15, 1992, Pat. No. 5,336,176, said Ser. No. 247,205, is a division of Ser. No. 800,507, Nov. 27, 1991, abandoned.

[51] Int. Cl.$^6$ ............................................. A61M 5/32
[52] U.S. Cl. ........................... 604/174; 604/164; 606/185; 606/198
[58] Field of Search ................................... 604/105, 107, 604/108, 109, 164, 165, 174; 606/1, 185, 198

[56] References Cited

U.S. PATENT DOCUMENTS

| | | | |
|---|---|---|---|
| 4,535,773 | 8/1985 | Yoon | 604/51 |
| 4,610,242 | 9/1986 | Santangelo et al. | 600/114 |
| 4,655,219 | 4/1987 | Petruzzi | 606/206 |
| 4,994,079 | 2/1991 | Genese et al. | 606/206 |
| 5,002,557 | 3/1991 | Hasson | 604/174 |
| 5,116,353 | 5/1992 | Green | 606/184 |
| 5,122,122 | 6/1992 | Allgood | 604/174 |
| 5,147,316 | 9/1992 | Castillenti | 604/164 |
| 5,147,378 | 9/1992 | Markham | 606/206 |
| 5,152,754 | 10/1992 | Plyley et al. | 604/164 |
| 5,158,552 | 10/1992 | Borgia et al. | 604/165 |
| 5,176,697 | 1/1993 | Hasson et al. | 604/174 |
| 5,197,971 | 3/1993 | Bonutti | 606/192 |
| 5,217,451 | 6/1993 | Freitas | 604/174 |
| 5,226,426 | 7/1993 | Yoon | 604/165 X |
| 5,232,451 | 8/1993 | Freitas et al. | 604/174 |
| 5,267,960 | 12/1993 | Hayman et al. | 604/174 |
| 5,273,529 | 12/1993 | Idowu | 604/174 |
| 5,290,243 | 3/1994 | Chodorow et al. | 604/165 |
| 5,290,249 | 3/1994 | Foster et al. | 604/174 |
| 5,290,304 | 3/1994 | Storace | 606/184 |
| 5,292,310 | 3/1994 | Yoon | 604/158 |
| 5,295,993 | 3/1994 | Green | 606/184 |
| 5,312,354 | 5/1994 | Allen et al. | 604/157 |
| 5,318,580 | 6/1994 | Gresl, Jr. | 606/185 |
| 5,318,585 | 6/1994 | Guy et al. | 606/185 |
| 5,320,610 | 6/1994 | Yoon | 604/158 |
| 5,324,268 | 6/1994 | Yoon | 604/158 |
| 5,330,432 | 7/1994 | Yoon | 604/164 |
| 5,336,176 | 8/1994 | Yoon | 604/51 |
| 5,338,305 | 8/1994 | Plyley et al. | 604/164 |
| 5,346,459 | 9/1994 | Allen | 606/185 |

(List continued on next page.)

*Primary Examiner*—Sam Rimell
*Assistant Examiner*—Robert V. Racunas

[57] ABSTRACT

A safety penetrating instrument for penetrating an anatomical cavity wall to gain access to an anatomical cavity includes a cannula, a penetrating member disposed in the cannula and movable relative to the cannula between a penetrating position where the tissue penetrating distal end of the penetrating member protrudes distally from the distal end of the cannula and a protected position where the penetrating member distal end is proximally spaced from the distal end of the cannula, a retracting mechanism for moving the penetrating member proximally from the penetrating position to the protected position and for permitting the penetrating member to move distally to the penetrating position, a locking mechanism for locking the penetrating member in the penetrating position, a spring strip mounted by the penetrating member and having an extendable portion movable inwardly in a lateral direction transverse to a longitudinal axis of the penetrating member from an extended position to a retracted position during penetration of the anatomical cavity wall and outwardly in the lateral direction from the retracted position to the extended position upon introduction of the extendable portion in the anatomical cavity, and a releasing mechanism responsive to movement of the extendable portion from the retracted position to the extended position for triggering release of the locking mechanism to permit the retracting mechanism to move the penetrating member to the protected position.

15 Claims, 6 Drawing Sheets

U.S. PATENT DOCUMENTS

| | | | |
|---|---|---|---|
| 5,350,393 | 9/1994 | Yoon | 606/185 |
| 5,360,405 | 11/1994 | Yoon | 604/165 |
| 5,378,239 | 1/1995 | Termin et al. | 604/174 |
| 5,401,247 | 3/1995 | Yoon | 604/165 |
| 5,423,760 | 6/1995 | Yoon | 604/165 |
| 5,423,770 | 6/1995 | Yoon | 604/281 |
| 5,431,635 | 7/1995 | Yoon | 604/165 |
| 5,445,617 | 8/1995 | Yoon | 604/165 |
| 5,466,224 | 11/1995 | Yoon | 604/165 |
| 5,478,317 | 12/1995 | Yoon | 604/165 |
| 5,549,595 | 8/1996 | Freitas | 604/174 |
| 5,634,934 | 6/1997 | Yoon | 606/185 |

RETRACTABLE SAFETY PENETRATING INSTRUMENT WITH LATERALLY EXTENDABLE SPRING STRIP

CROSS-REFERENCE TO RELATED APPLICATIONS

This application is a continuation-in-part of application Ser. No. 08/247,205, filed May 20, 1994 now U.S. Pat. No. 5,634,934, and application Ser. No. 08/079,586, filed Jun. 22, 1993. Application Ser. No. 08/247,205 is a division of application Ser. No. 07/800,507, filed Nov. 27, 1991, which is now abandoned. Application Ser. No. 08/079,586 is a division of application Ser. No. 07/868,578, filed Apr. 15, 1992, now U.S. Pat. No. 5,336,176. The disclosures of the above patent applications are incorporated herein by reference.

BACKGROUND OF THE INVENTION

1. Field of the Invention

The present invention pertains to penetrating instruments for penetrating walls of anatomical cavities and, more particularly, to penetrating instruments having retractable penetrating members biased to a retracted position such that tissue and organ structures are protected from the tips of the penetrating members.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laproscopic procedures in the abdominal cavity. Such penetrating instruments typically include a cannula or portal sleeve and a penetrating member, such as a trocar, disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring-biased to protrude distally beyond the tip of the penetrating member in response to the reduced axial force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While safety penetrating instruments have been well received, there is room for improvement in minimizing the likelihood of the penetrating member being retracted before the cannula has entered the anatomical cavity in that distal movement of a triggering component of the safety penetrating instrument can be induced prematurely in response to a reduction in the axial force acting on the distal end of the triggering component caused by irregular or uneven advancement of the safety penetrating instrument through the anatomical cavity wall.

SUMMARY OF THE INVENTION

Accordingly, it is a primary object of the present invention to improve safety penetrating instruments of the type having a retractable penetrating member disposed within a cannula.

Another object of the present invention is to prevent premature retraction of a penetrating member of a safety penetrating instrument in response to axial forces caused by irregular or uneven advancement of the safety penetrating instrument through an anatomical cavity wall.

A further object of the present invention is to trigger retraction of a penetrating member of a safety penetrating instrument in response to lateral movement of a spring strip caused by a reduction in lateral force from tissue contact upon penetration into an anatomical cavity.

The present invention has an additional object to utilize lateral movement of a spring strip from a contracted position within a penetrating member of a safety penetrating instrument to an extended position disposed externally of the penetrating member to trigger retraction of the penetrating member.

Some of the advantages of the present invention are that the safety penetrating instrument minimizes the likelihood of the penetrating member being retracted before the cannula has entered the anatomical cavity, that the reliability of safety penetrating instruments is improved by reducing the number of moving parts needed to trigger retraction of the penetrating member, that retraction of the penetrating member is made possible even in cases where distally biased movement of a triggering component is contraindicated, and that the safety penetrating instrument of the present invention can be inexpensively manufactured with minimum components to reduce costs, facilitate sterilization for reuse and allow economical, single patient use.

The present invention is generally characterized in a safety penetrating instrument for penetrating an anatomical cavity wall to gain access to an anatomical cavity including a cannula having a distal end for being disposed in the anatomical cavity and a proximal end for being disposed externally of the anatomical cavity, a penetrating member disposed in the cannula and having a longitudinal axis, retracting means for moving the penetrating member proximally from a penetrating position where a tissue penetrating distal end of the penetrating member protrudes distally from the distal end of the cannula to a protected position where the distal end of the penetrating member is proximally spaced from the distal end of the cannula, a locking mechanism for locking the penetrating member in the penetrating position, a spring strip mounted by the penetrating member including an extendable portion movable inwardly in a lateral direction transverse to the longitudinal axis from an extended position to a retracted position during penetration of the anatomical cavity wall and outwardly in the lateral direction from the retracted position to the extended position upon introduction of the probe into the anatomical cavity, and a releasing mechanism including a mechanical trigger member operatively associated with the locking mechanism for triggering release of the locking mechanism in response to mechanical engagement of an operating member with the trigger member caused by lateral movement of the extendable portion from the retracted position to the extended position.

The above and still further objects, features and advantages of the present invention will become apparent from the following description of the preferred embodiments when considered in conjunction with the accompanying drawings wherein like reference numerals or reference numerals sharing the same last two digits are utilized to designate like components.

DESCRIPTION OF THE PREFERRED EMBODIMENTS

The safety penetrating instrument of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the safety penetrating instrument of the present invention can be used for safe penetration or introduction into anatomical cavities of needles with fluid flow therethrough and catheters as well as for other instruments engaging tissue during surgical or diagnostic procedures. Accordingly, the cannula or outer tubular member of the safety penetrating instrument can be a portal sleeve, a needle, a catheter or a tubular component of a medical instrument.

Figure 1:
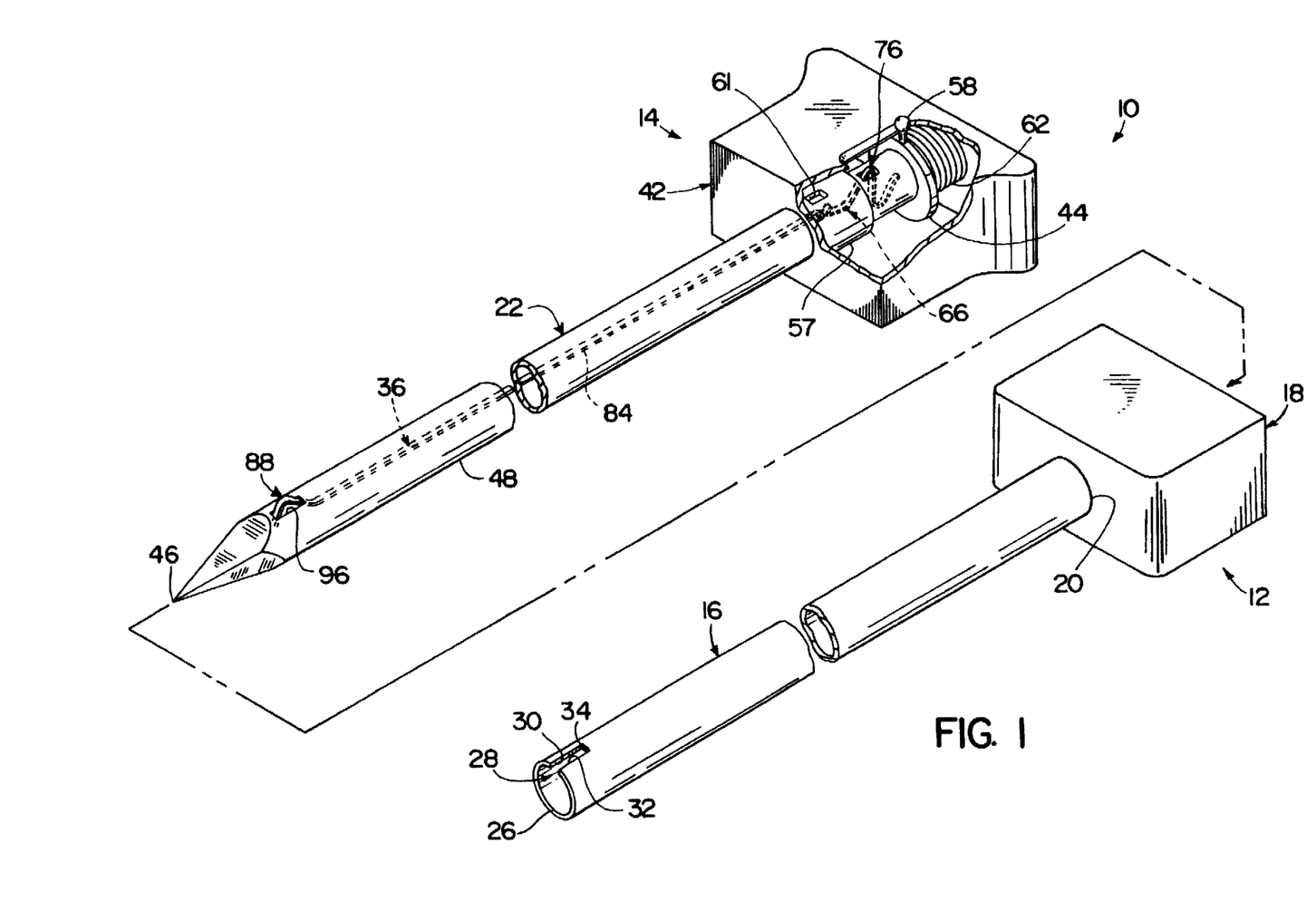
FIG. 1 is an exploded perspective view of a penetrating instrument according to the present invention.
Figure 2:
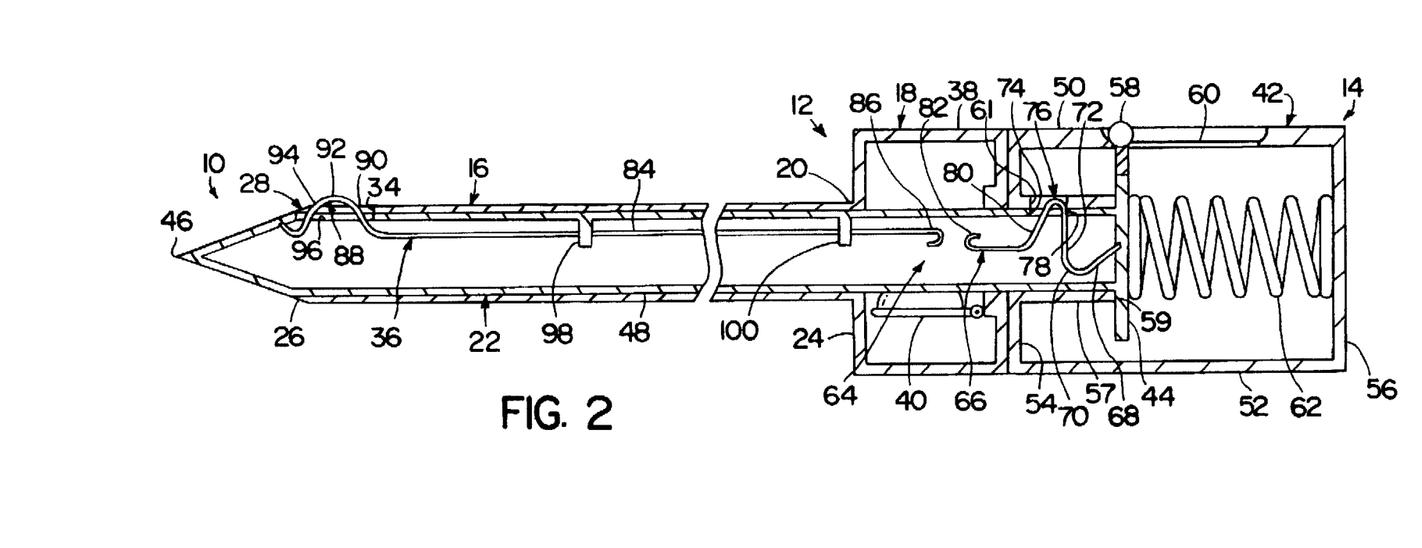
FIG. 2 is a broken side view, partly in section, of the penetrating instrument of FIG. 1.

A penetrating instrument 10 according to the present invention, as shown in FIGS. 1 and 2, is formed of a portal unit 12 and a penetrating unit 14. The portal unit 12 includes an elongate portal sleeve, cannula or catheter 16 and a housing 18 mounted at a proximal end 20 of the portal sleeve. Portal sleeve 16 and housing 18 of the portal unit can be made of any desirable medically acceptable materials depending on procedural use and desirability of being for single patient use or reusable and can be of integral one-piece construction as shown or formed separately and joined together. Portal sleeve 16 is preferably cylindrical or tubular in configuration to define a lumen for receiving a penetrating member 22 of the penetrating unit. Proximal end 20 of the portal sleeve is secured to a front wall 24 of housing 18. Distal end 26 of the portal sleeve includes at least one longitudinally extending slot 28 having a pair of circumferentially spaced longitudinal edges 30 and 32 extending in parallel from the distal end of the portal sleeve to a transverse edge 34 extending circumferentially between the longitudinal edges. The distance that the slot 28 extends longitudinally along the portal sleeve or, in other words, the length of slot 28, is dependent on the configuration of a laterally extendable spring strip 36 of the penetrating instrument 10 in the extended position as will be explained further below. As best seen in FIG. 2, slot 28 has a length to align a laterally extendable portion of the spring strip with the distal end of the portal sleeve. It will be appreciated that the circumferential location of the slot about the distal end of the portal sleeve can be varied as desired and that the width of the slot will be dependent on the width of the spring strip as described more fully below. As shown in FIG. 1, slot 28 is formed along or in alignment with a longitudinal axis of the portal sleeve on a side of the portal sleeve corresponding to a top wall 38 of the housing.

Housing 18 of the portal unit is preferably constructed to sealingly engage instruments passing therethrough and to include a valve 40 biased to a closed state when no instrument passes through the portal sleeve. Valve 40 is shown as a flapper valve; however, any suitable valve construction can be utilized including, for example, trumpet or nipple valves. Housing 18 can have any desirable configuration in cross-section to facilitate grasping by the surgeon and can have various valves, stopcocks and seals to control fluid flow therethrough as well as various adapters to adjust to the size of instruments inserted through the portal unit.

Penetrating unit 14 includes penetrating member 22 and a hub 42 mounting a proximal end of the penetrating member. Penetrating member 22 includes a round flange 44 at a proximal end, a sharp distal end or tip 46 and a hollow tubular body 48 extending between the proximal and distal ends. The penetrating member distal end can have any configuration desired by a surgeon for a particular procedure including, for example, the solid pyramidal trocar configuration shown or conical, threaded, multifaceted or open, slanted or needle configuration. The penetrating member can be made of any suitable, medical grade materials and can be made of multiple components such that, for example, the distal tip can be made of stainless steel and secured in any conventional manner, such as by threads, to the distal end of the body, which can be tubular and made of a less expensive material, such as plastic or metal. Hub 42 can have any desired external configuration to facilitate grasping of the portal unit and the penetrating unit by the surgeon with one hand. As best seen in FIG. 2, hub 42 includes a top wall 50 and bottom wall 52 in configuration parallel to a longitudinal axis of the penetrating instrument, a front wall 54 and rear wall 56 extending transversely between top and bottom walls 50 and 52, and a cylindrical guide tube 57 extending from an opening in the front wall toward the rear wall. Penetrating member 22 extends through guide tube 57 to terminate at flange 44 which is disposed between a proximal end 59 of the guide tube and the rear wall of the hub. Flange 44 of the penetrating member is coupled with a handle 58 movable along a slot or opening 60 formed in the top wall of the hub in a direction parallel with the longitudinal axis of the penetrating instrument. A retracting member 62 is mounted between flange 44 and rear wall 56 of the hub to bias the penetrating member in a proximal direction to a retracted or protected position where distal end 46 of the penetrating member is proximally spaced from the distal end of the portal sleeve. Retracting member 62 can include a helical coil spring mounted in tension between flange 44 and rear wall 56 of the hub as shown or any other type of spring or other bias device including, for example, tension springs, compression springs, torsion springs, pan springs, pivotally connected members, rubber, plastic or magnets.

A locking and releasing mechanism 64 for locking the penetrating member in an extended penetrating position exposing the sharp distal tip of the penetrating member and for releasing the penetrating member to allow the penetrating member to move to the retracted position is disposed within penetrating member 22. Locking and releasing mechanism 64 includes a latch or locking spring 66, made of a strip of resilient material, formed to have a base or stem 68 extending distally from flange 44 to a bend 70 joining the base with an upwardly angled arm 72. Arm 72 extends through an opening or slot 74 formed in the tubular body of penetrating member 22 to form a latch 76 having a proximal latching surface 78 disposed substantially transverse to the longitudinal axis of the penetrating instrument and a distal latching surface 80 extending downwardly at an angle from the proximal latching surface toward the longitudinal axis of the penetrating instrument where a trigger member in the form of an upwardly turned portion or hook 82 is formed. In the extended penetrating position shown in FIG. 1, flange 44 abuts the proximal end of guide tube 57 and latch 76 engages a slot 61 formed in the cylindrical side wall of guide tube 57 in alignment with slot 74 of the penetrating member to lock the penetrating member in the extended position.

Spring strip 36, which serves as a triggering component for releasing locking spring 66, is preferably made of a strip of resilient material formed to have a straight central portion 84 disposed within the penetrating member along a longitudinal axis thereof, a downwardly turned proximal portion or hook 86 and a laterally expandable or extendable distal portion 88. Extendable distal portion 88 is biased in a direction radially outward or transverse to the longitudinal axis of the penetrating member so as to be normally disposed in the laterally extended position shown in FIGS. 1 and 2. In the laterally extended position, the extendable distal portion 88 of the spring strip forms a generally U-shaped projection having a first leg 90 extending transversely from straight central portion 84 to a bend or apex 92 disposed outwardly of the periphery, circumference or cross-section of the penetrating member and portal sleeve, and a second leg 94 extending inwardly from the apex to be fixed to an inside surface of the penetrating member. A slot or opening 96 is formed in the penetrating member in alignment with slot 28 at the distal end of the portal sleeve to permit passage of the extendable distal portion through the penetrating member and portal sleeve in the extended position.

Central portion 84 of the spring strip passes through eyelets 98 and 100 mounted on an inside surface of the penetrating member to permit sliding movement of the central portion of the spring strip within the penetrating member when the extendable distal portion 88 is depressed or flattened and to assure axial alignment of the downwardly turned portion or hook 86 of the spring strip with the upwardly turned portion or hook 82 at the distal end of the locking spring. Since the distal end of the spring strip is fixed, it will be appreciated that depression or flattening of extendable portion 88 of the spring strip causes an axial extension of the spring strip in the proximal direction; and, as best seen in FIG. 2, when extendable portion 88 is in the laterally extended position, downwardly turned portion 86 of the spring strip is axially spaced from upwardly turned portion 82 of the locking spring a predetermined distance preferably corresponding to the axial extension resulting from depression or flattening of the laterally extendable portion.

Figure 3:
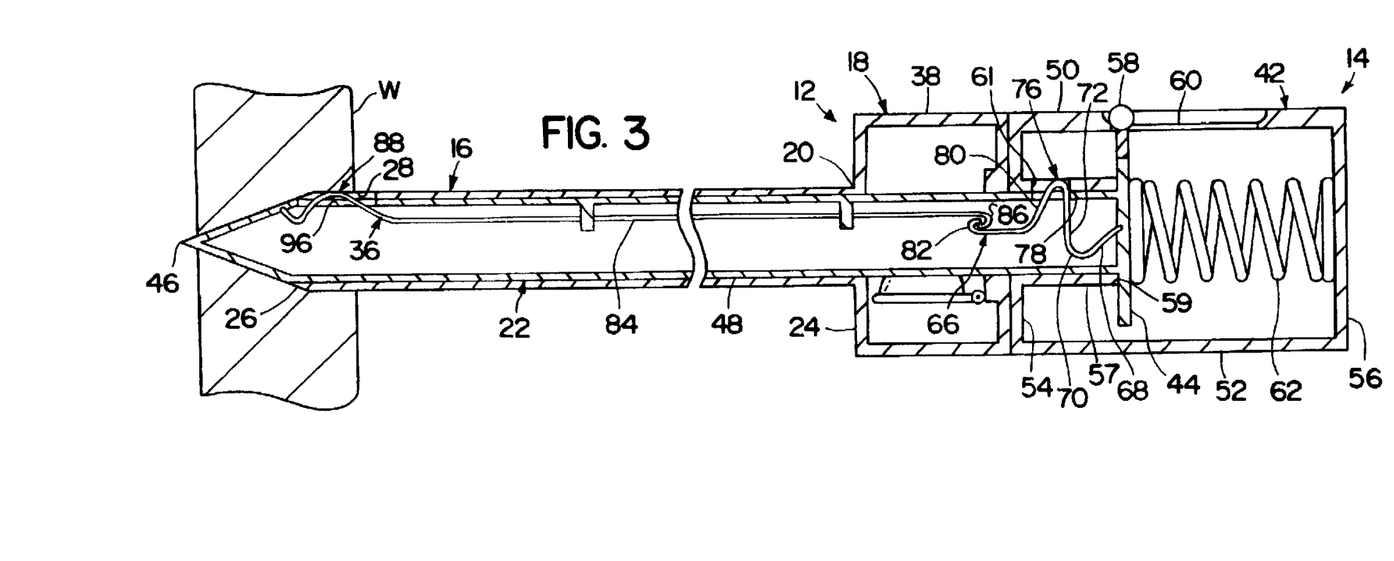
FIG. 3 is a broken side view, partly in section, of the penetrating instrument of FIG. 1 during penetration of an anatomical cavity wall.

The outward bias for extendable portion 88 can be selected to permit movement of the extendable portion inwardly toward the instrument longitudinal axis in the lateral, radial or transverse direction from the extended position to the retracted position shown in FIG. 3 in response to a lateral resistance or force from anatomical tissue during penetration of an anatomical cavity wall and to permit movement of the extendable portion outwardly in the lateral, radial or transverse direction from the retracted position to the extended position in response to a decrease, reduction or removal of the lateral resistance or force upon penetration into the cavity. In the retracted position, extendable portion 88 is flattened or straightened so as to be disposed parallel to or in alignment with the longitudinal axis of the instrument such that the extendable portion has an axial length in the retracted position greater than the length of the extendable portion in the extended position. Accordingly, movement of extendable portion 88 from the extended to the retracted position causes the central portion of the spring strip and, therefore hook 86 at the proximal end of the central portion, to move proximally relative to penetrating member 22 as shown in FIG. 3, and movement of extendable portion 88 from the retracted position to the extended position causes central portion 84 and hook 86 to move distally relative to the penetrating member. Additionally, in the retracted position, the radius, height or lateral extent of the extendable portion is aligned or substantially aligned with the periphery, circumference or cross-section of the portal sleeve to facilitate passage of the portal sleeve through anatomical tissue.

The outward bias for extendable portion 88 can be provided in many various ways such as by forming the spring strip of a resilient material or a material having shape memory, such that the outward bias is provided by the spring strip itself, or by utilizing a separate bias device disposed between the spring strip and an inside surface of the penetrating member. Alternatively, the outward bias for extendable portion 88 can be provided by forming the spring strip of multiple pivoting segments or linkages and biasing the segments using torsion springs or the like. The extendable portion 88 could also be formed by a button or plunger biased to protrude laterally from the penetrating member and coupled by means of cams or gears with the central portion of the spring strip to produce axial or longitudinal movement of the spring strip in response to lateral movement of the button.

The portal unit 12 and the penetrating unit 14 can be provided to a surgeon separately or assembled together as shown in FIG. 2, and either or both of the portal and penetrating units can be manufactured in a manner to be disposable for single patient use or to be sterilizable for reuse. The hub 42 can be coupled to the housing 18 by any suitable detent or latch mechanisms if desired, and the penetrating unit 14 can be withdrawn from the portal unit 12 leaving the portal sleeve 16 in place within an anatomical cavity.

Portal unit 12 and penetrating unit 14 of the penetrating instrument 10 are preferably provided to the surgeon separately as shown in FIG. 1 and are assembled prior to use. In the unassembled condition shown in FIG. 1, penetrating member 22 is preferably in a retracted position wherein retracting member 62 is in a relaxed state and flange 44 is proximally spaced from guide tube 57. As a result, handle 58 is disposed at the proximal end of slot 60 and the latch 76 formed by locking spring 66 is made to extend through slot 74 in the penetrating member to be disposed proximally of guide tube 57. Furthermore, in the unassembled condition shown, spring strip 36 is in the extended position wherein the extendable portion 88 of the spring strip projects or protrudes laterally from the body of the penetrating member and the operating member formed by hook 86 of the spring strip is distally spaced from the trigger member formed by hook 82 of the locking spring.

Figure 5:
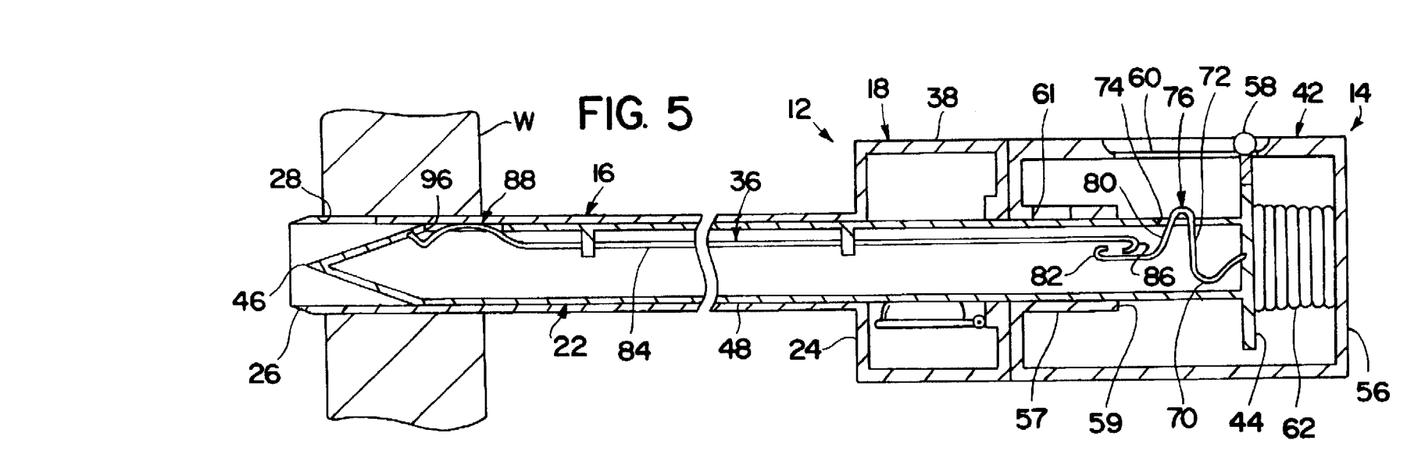
FIG. 5 is a broken side view, partly in section, of the penetrating instrument of FIG. 1 following retraction of the penetrating member.

When a surgeon desires to penetrate into an anatomical cavity using the penetrating instrument 10, the portal unit 12 and penetrating unit 14 of the penetrating instrument are assembled as shown in FIG. 5 by sliding penetrating member 22 through the portal housing until the front wall of hub 42 abuts the rear wall of housing 18. During assembly of the penetrating instrument, extendable portion 88 of the spring strip will be moved laterally inward from the extended position to a compressed, flattened or retracted position within the portal sleeve as shown in FIG. 5. Movement of extendable portion 88 from the extended position to the retracted position causes axial or longitudinal movement of the central portion of the spring strip toward the proximal end of the instrument such that hook 86 formed at the proximal end of the spring strip is made to overlap hook 82 formed at the distal end of the locking spring. In the assembled condition, penetrating member 22 is disposed within portal sleeve 16 and distal end 46 of the penetrating member is in a protected position proximally spaced from portal sleeve distal end 26.

Figure 6:
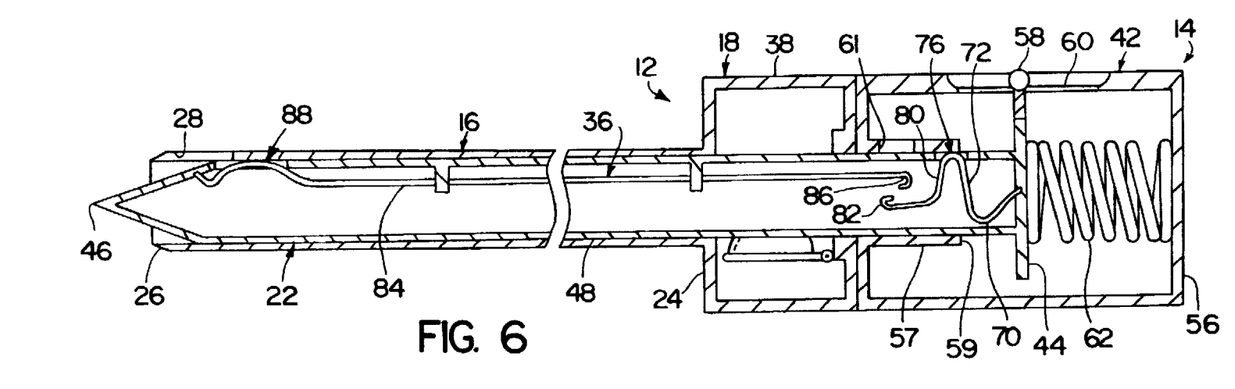
FIG. 6 is a broken side view, partly in section, of the penetrating instrument of FIG. 1 illustrating movement of the penetrating member to the extended position.

Penetrating member 22 can be moved from the protected or retracted position shown in FIG. 5 to the extended or penetrating position shown in FIG. 2 by sliding handle 58 along slot 60 in a distal direction until flange 44 of the penetrating member abuts the proximal end of guide tube 57. As handle 58 is advanced distally, flange 44 is also moved distally causing penetrating member 22 to slide within portal sleeve 16 and distal latching surface 80 of locking spring 66 to come into contact with or engage guide tube 57. Pressure exerted on distal latching surfacing 80 by the guide tube causes locking spring 66 to resiliently deform inwardly and to be held in the deformed position so long as latch 76 is disposed within the guide tube as shown in FIG. 6. In the deformed position, hook 82 at the distal end of locking spring 66 is deflected or moved out of axial alignment with hook 86 of spring strip 36 to prevent latching engagement of the hooks when the central portion of the spring strip moves distally in response to lateral extension of extendable portion 88. Extension of extendable portion 88 occurs when slot 96 at the distal end of the penetrating member becomes aligned with slot 24 formed at the distal end of the portal sleeve. At about the same time, or shortly thereafter, slot 74 at the proximal end of penetrating member becomes aligned with slot 61 in the guide tube so that locking spring 66 can assume its normal locking position wherein proximal latching surface 78 abuts the proximal end of slot 61 to prevent proximal movement of the penetrating member under the influence of retracting member 62.

Figure 4:
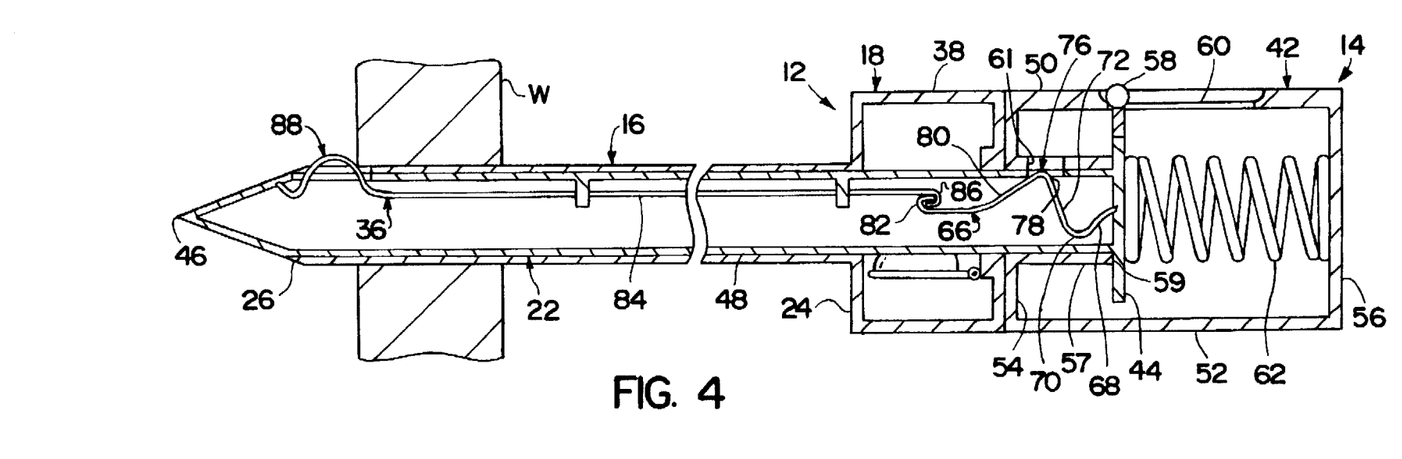
FIG. 4 is a broken side view, partly in section, of the penetrating instrument of FIG. 1 immediately upon penetrating into the anatomical cavity.

With the penetrating instrument 10 in the condition illustrated in FIG. 2, penetrating member 22 is locked in the extended penetrating position wherein the distal end of the penetrating member protrudes beyond the distal end of the portal sleeve 16 and spring strip 36 is in the extended position wherein extendable portion 88 protrudes laterally beyond the outer circumference, periphery or cross-section of the portal sleeve. When the sharp distal end 46 of the penetrating member is brought into contact with tissue forming an anatomical cavity wall W, the force-to-penetrate is limited to the force required to cause the sharp distal end to pass through the cavity wall W, and the portal sleeve and the penetrating member do not move longitudinally during penetration. As penetration continues, a force from the anatomical tissue surrounding the portal sleeve 16 will depress, flatten or contract the extendable portion 88 of spring strip 36 causing movement of the extendable portion from the extended position to the retracted position as shown in FIG. 3 to facilitate movement of portal sleeve 16 through the anatomical cavity wall. Movement of extendable portion 88 from the extended position to the retracted position causes longitudinal or axial movement of central portion 84 in a proximal direction until the operating member formed by hook 86 at the proximal end of the spring strip slides over the trigger member formed by hook 82 at the distal end of locking spring 66 to assume a latched position wherein the hooks are mechanically coupled or interlocked such that distal movement of the central portion of the spring strip will result in a distal force being applied to the locking spring. Once the extendable portion 88 has passed through the anatomical cavity wall W, the force from tissue contact will be reduced, decreased or removed permitting extendable portion 88 to move from the retracted position to the extended position due to the bias of the spring strip as shown in FIG. 4. Movement of extendable portion 88 from the retracted position to the extended position causes longitudinal or axial distal movement of central portion 84 relative to the penetrating member such that the operating member formed by hook 86 exerts a distal force against the trigger member formed by hook 82 causing locking spring 66 to be pulled in a distal direction and thereby flattened or straightened in such a way that latch 76 is disposed within the guide tube 57 and no longer in latching engagement with slot 61 formed in the guide tube. Retracting member 62 will then move the penetrating member 22 from the extended penetrating position to the retracted position shown in FIG. 5 wherein the distal end of penetrating member 22 is disposed within the portal sleeve and handle 58 is disposed at the proximal end of slot 60. The penetrating unit 14 can then be withdrawn from the portal unit 12 leaving the portal sleeve 16 in place such that instruments for performing endoscopic procedures can be introduced into the cavity via the portal formed by the portal unit.

The penetrating instrument of the present invention can be modified in various ways to protect or shield medical personnel from the sharp distal end of the penetrating member upon withdrawal of the penetrating unit from the portal unit following penetration into an anatomical cavity. For example, the modified penetrating instrument 110 shown in FIG. 7 includes a penetrating unit 114 similar to penetrating unit 14 but with a protective sheath 101 disposed concentrically around the penetrating member and fixed at one end to hub 142 of the penetrating unit. Protective sheath 101 has a proximal end 103 secured to a front wall 154 of the hub and a distal end 105. The distance between proximal and distal ends 103 and 105 of the protective sheath or, in other words, the length of protective sheath 101, is chosen such that the distal end of penetrating member 22 will protrude distally from the protective sheath when in the extended position and will be protected or shielded by the protective sheath when in the retracted position. A slot or opening 107, similar in size to slot 196 in the penetrating member, is formed at the distal end of protective sheath 101 to permit lateral movement of the extendable portion of spring strip 136 between retracted and extended positions as described above in connection with penetrating instrument 10. Portal unit 112 for penetrating instrument 110 is identical to portal unit 12 for penetrating instrument 10 with the possible exception of any modification in size needed to accommodate passage of the protective sheath through the portal unit.

Figure 7:
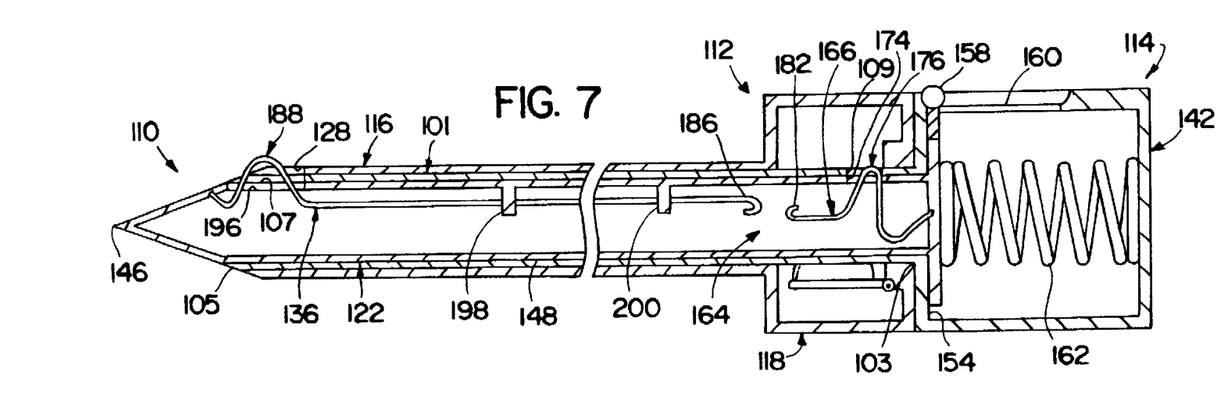
FIG. 7 is a broken side view, partly in section, of a modified penetrating instrument according to the present invention.

FIG. 7 also illustrates a modified locking and releasing mechanism 164 wherein the locking spring 166 of the locking and releasing mechanism is made to latch against or engage other parts of the penetrating unit to lock the penetrating member in the extended position. For example, in FIG. 7, the latching portion 176 of the locking spring extends through a second slot or opening 109 formed in the protective sheath near the proximal end of the sheath, thereby obviating the need for a guide tube disposed within the hub.

Various other locking and releasing mechanisms can be used to lock the penetrating member in the extended position and to release the penetrating member to be moved to the retracted position in response to laterally biased movement of an extendable portion at the distal end of the penetrating member. For example, the penetrating instrument 210 illustrated in FIG. 8 includes a penetrating unit 214 similar in most respects to the other penetrating units described above but with a modified locking and releasing mechanism 264. Locking and releasing mechanism 264 includes a generally V-shaped locking spring 266 having a pair of opposed arms 267 and 269 angled outwardly from opposed ends of a partly circular base 270 in a direction away from the instrument longitudinal axis. Arms 267 and 269 carry or form latches 271 and 273 having distal latching surfaces extending inwardly from the arms in the direction of the longitudinal axis to engage flange 244 of the penetrating member in the extended position. Latches 271 and 273 connect with a pair of generally L-shaped extensions or hooks 275 and 277 having longitudinal portions 279 and 281, respectively, extending transversely from the distal latching surfaces in a distal direction and inwardly turned portions 283 and 285, respectively, extending toward one another.

Figure 8:
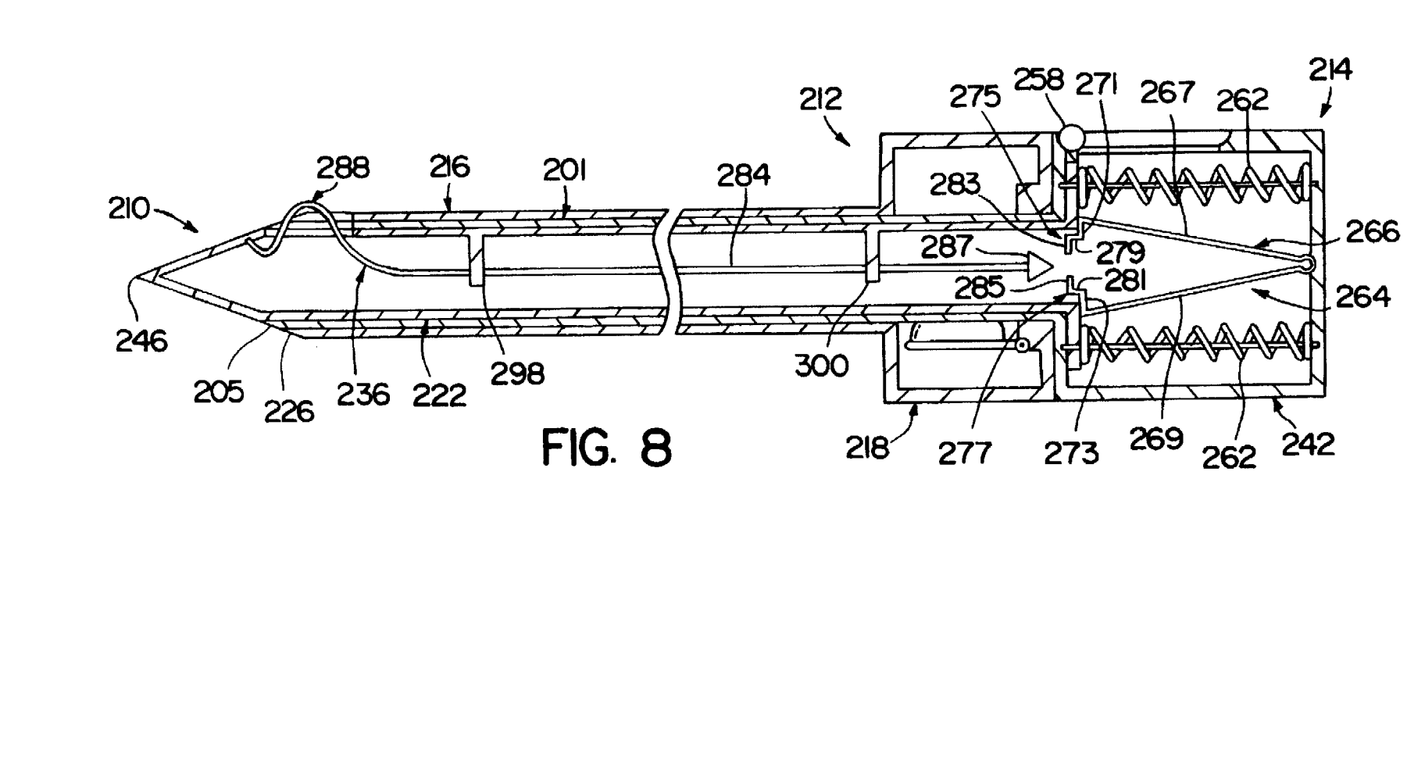
FIG. 8 is a broken side view, partly in section, of another modification of a penetrating instrument according to the present invention.

Spring strip 236 of the penetrating instrument is similar to the spring strip previously described but is modified to include an operating member in the form of an enlarged tapered portion or pawl 287 at a proximal end of the spring strip for operatively engaging the trigger members formed by the L-shaped hooks of the locking spring to release the penetrating member from the locked extended position. Tapered portion 287 is shown with a conical surface tapering inward toward a proximal end of the instrument; it will be appreciated, however, that other geometric configurations can be used to form the tapered portion including, for example, wedge shaped and frustoconical geometric configurations.

Prior to use, penetrating member 222 of the modified penetrating instrument is preferably in a retracted position wherein the distal end of the penetrating member is disposed within protective sheath 201, and locking spring 266 is disposed within the penetrating member in a deflected position where arms 267 and 269 of the spring are pivoted toward one another. When a surgeon desires to penetrate into an anatomical cavity, penetrating member 222 is placed in the extended position by operation of a handle 258 in the manner previously described. Since the base 270 of locking spring 266 is fixed within the hub, distal movement of penetrating member 222 relative to the hub permits the locking spring 266 to spring outward and snap into place behind the penetrating member flange 244 when the penetrating member assumes the extended position shown. It should be noted, however, that the length of the slots through which the extendable portion 288 protrudes as well as the length of arms 267 and 269 are chosen such that the extendable portion will be able to move from the retracted position to the extended position prior to the arms being released from within the penetrating member. This assures that tapered portion 287 of the probe will be distally spaced from locking spring 266 when the locking spring ultimately snaps into place.

Penetrating member 222 is held in the extended position against the influence of retracting members 262 by engagement of flange 244 with the distal latching surfaces formed by latches 271 and 273 of the locking spring. During penetration of an anatomical cavity wall, extendable portion 288 of spring strip 236 moves from the extended position to the retracted position and, as a result, the operating member formed by the tapered portion 287 at the proximal end of the spring strip is moved axially in the proximal direction past inwardly turned portions 283 and 285 of the locking spring. As the tapered portion 287 moves past the inwardly turned portions 283 and 285 of the locking spring, the arms of the locking spring are cammed outwardly away from the longitudinal axis of the instrument to allow the tapered portion of the spring strip to move proximally past the inwardly turned portions. With the tapered portion 287 disposed proximally of the inwardly turned portions of the locking spring, arms 267 and 269 of the locking spring move inward somewhat to the original locking position shown in FIG. 7 placing the inwardly turned portions of the spring in the axial or longitudinal path of the tapered portion. Upon penetration into the anatomical cavity, extendable portion 288 of the spring strip moves from the retracted position to the extended position and tapered portion 287 is pulled in the distal direction so that the flat distal edge of the tapered portion contacts the inwardly turned portions of the spring to flatten or straighten the spring. As the locking spring is straightened, arms 267 and 269 are pivoted toward one another releasing flange 244 from contact with latches 271 and 273. Penetrating member 222 then moves proximally under the influence of retracting members 262 to the retracted position, after which the penetrating unit can be removed from the portal unit as described above.

The outward bias of the extendable portion of the spring strip need only be great enough to produce slight longitudinal or axial movement of the operating member past the trigger member portion of the locking spring such that force-to-penetrate can be minimized. With the present invention, retraction of the penetrating member can be triggered by lateral movement of the extendable portion of the spring strip from a retracted position to an extended position upon penetration through an anatomical cavity wall without requiring longitudinal movement of the penetrating member, the portal sleeve or a safety member or probe. The extendable portion of the spring strip can have any configuration to be moved inwardly in response to the force from tissue contact including curved and angularly bent configurations. Additionally, the extendable portion can be located at various locations along the length of the penetrating member to trigger retraction of the penetrating member in response to various predetermined distances of protrusion for the penetrating member. For example, when the extendable portion is located adjacent the distal end of the portal sleeve, retraction of the penetrating member will not occur until the portal sleeve has entered the anatomical cavity. In the case of small cavities, such as veins and arteries, it is sometimes desirable to retract the penetrating member before it can penetrate through the other side of the cavity so that placement of the extendable portion at or near the penetrating tip of the penetrating member may be desired. Furthermore, a number of extendable portions can be formed along the length of a single spring strip and/or multiple spring strips can be disposed within the penetrating member to achieve sequential retraction and extension of the extendable portions and/or redundant triggering of the release mechanisms.

The components of the penetrating instrument of the present invention can be made of any suitable, medical grade materials to permit sterilization for reuse or for single patient use. The components can be made of multiple parts of various configurations and materials to reduce costs. The portal unit can have various valves, stopcocks and seals in the housing to control fluid flow therethrough and various adapters to adjust to the size of instruments inserted through the portal unit. Conventional detent mechanisms can be used to connect the housing with the hub when the portal unit and the penetrating unit are assembled.

The locking and releasing mechanisms require only a latch for locking the penetrating member in the extended position and a trigger for releasing the latch in response to distal movement of an operating member carried by the probe; and, thus, it will be appreciated that various mechanism can be employed to produce the locking and releasing functions such as, for example, multiple movably or pivotally mounted cams or pawls. It will be appreciated that the locking and releasing mechanism can be designed and arranged in the penetrating member or hub in various ways to minimize the length of the hub and, therefore, the overall length of the instrument. Various locking and releasing mechanisms that can be simply modified for use in the penetrating instrument of the present invention are disclosed in U.S. Pat. Nos. 5,330,432; 5,324,268; 5,320,610; 5,336,176; and 5,360,405 to Yoon and applicant's pending applications Ser. No. 07/848,838, filed Mar. 10, 1992; Ser. No. 07/845,177, filed Sep. 15, 1992; Ser. No. 07/945,177, filed Sep. 15, 1992; Ser. No. 08/079,586, filed Jun. 22, 1993; Ser. No. 08/195,512, filed Feb. 14, 1994; Ser. No. 08/196,029, filed Feb. 14, 1994; Ser. No. 08/196,027, filed Feb. 14, 1994; Ser. No. 08/195,178, filed Feb. 14, 1994; Ser. No. 08/237,734, filed May 4, 1994; Ser. No. 08/247,205, filed May 20, 1994; Ser. No. 08/254,007, filed Jun. 3, 1994; and Ser. No. 08/260,439, filed Jun. 15, 1994. The disclosures of the above-listed issued patents and pending patent applications are incorporated herein by reference. The issued patents and pending applications listed above also disclose various bias arrangements useful with the penetrating instrument of the present invention. Other locking and releasing mechanisms that can be simply modified for use in the penetrating instrument of the present invention are disclosed in applicant's pending application Ser. Nos. 08/279,170 and 08/279,172, filed Jul. 22, 1994, the disclosures of which are incorporated herein by reference.

Figure 9:
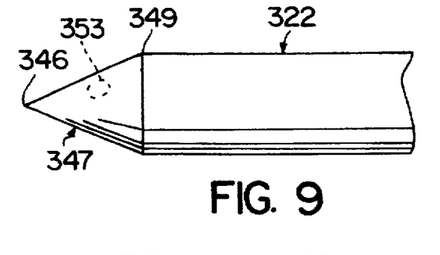
FIGS. 9–14 are fragmentary side views illustrating alternate distal end configurations for the penetrating member of the penetrating instrument according to the present invention.
Figure 10:
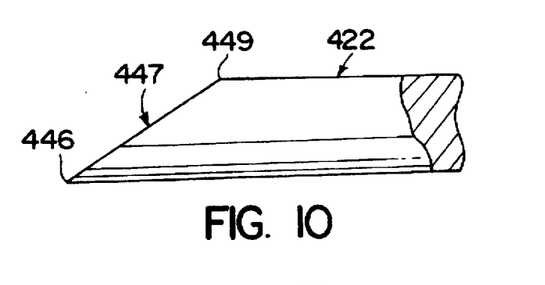
Figure 11:
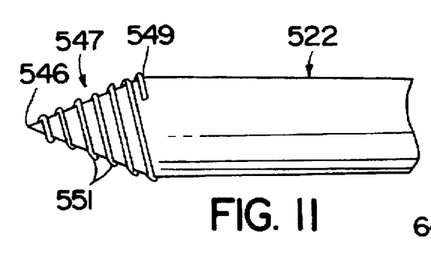
Figure 12:
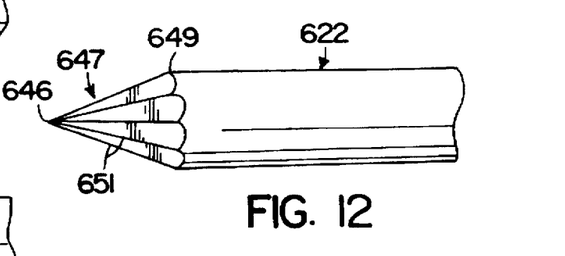
Figure 13:
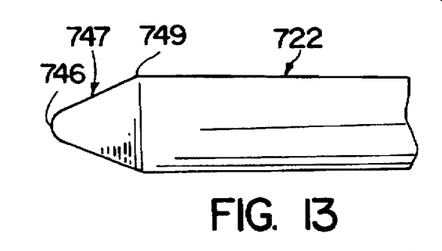
Figure 14:
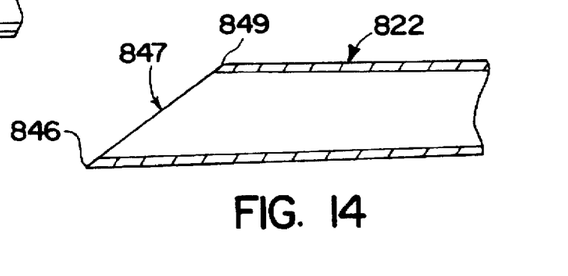

The distal end of the penetrating member for the penetrating instrument of the present invention can have any configuration desired for a particular procedure such as, for example, the pyramidal trocar configuration shown or a conical distal end 347 tapering from a junction 349 to a tip 346 as shown in FIG. 9, a beveled distal end 447 tapering from a junction 449 to a tip 446 as shown in FIG. 10, a screw-type distal end 547 having helical threads 551 extending from junction 549 to tip 546 as shown in FIG. 11, a multi-faceted distal end 647 having two or more facets 651 tapering from junction 649 to tip 646 as shown in FIG. 12, a blunt distal end 747 with a generally conical portion tapering from junction 749 to a rounded or flattened tip 746 as shown in FIG. 13, or a hollow tubular needle-like configuration with a beveled distal end 847 tapering from a junction 849 to a sharp tip 846 and defining a lumen with fluid flow therethrough as shown in FIG. 14. Additionally, the surface defining the distal end of the penetrating member can be irregular or smooth, continuous or disjointed, provided with cutting features or having any combination of the above. Any of the penetrating members shown and described herein can include a viewing port, like the viewing port shown in phantom at 353 in FIG. 9, for accommodating conventional optical viewing systems such as those utilizing fiber optics so that tissue can be visualized during penetration. It will also be appreciated that the distal end of the portal sleeve can be proximally spaced, distally spaced or aligned with the penetrating member junction from which the penetrating member distal end extends prior to penetrating an anatomical cavity wall. Furthermore, the penetrating member, portal sleeve and/or a safety member, such as a safety shield disposed between the penetrating member and the portal sleeve, can be mounted on bias members to permit proximal movement during penetration of an anatomical cavity wall and distal movement upon entering the anatomical cavity. Also, any distally-biased member can carry an operating member to trigger release of the penetrating member to move to the retracted position.

From the above, it will be appreciated that the penetrating instrument of the present invention minimizes the likelihood of the penetrating member being retracted before the portal sleeve or cannula has entered the anatomical cavity by utilizing a triggering component or spring strip that is substantially insensitive to changes in axial force caused by irregular or uneven advancement of the penetrating instrument through the anatomical wall. Instead, retraction of the penetrating member can be triggered in response to lateral movement of the spring strip caused by a reduction in lateral force from tissue contact upon penetration into an anatomical cavity.

The features of the various embodiments described above can be combined in any manner desired dependent upon the requirements and complexity of the penetrating instruments.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for penetrating an anatomical cavity wall to gain access to an anatomical cavity comprising a cannula having a distal end for being disposed in the anatomical cavity and a proximal end for being disposed externally of the anatomical cavity;

a penetrating member disposed in said cannula and having a longitudinal axis, said penetrating member being movable relative to said cannula between a penetrating position where a tissue penetrating distal end of said penetrating member protrudes distally from said distal end of said cannula and a protected position where said penetrating member distal end is proximally spaced from said distal end of said cannula;

retracting means for moving said penetrating member proximally from said penetrating position to said protected position and for permitting said penetrating member to move distally to said penetrating position;

a locking mechanism for locking said penetrating member in said penetrating position;

a spring strip mounted by said penetrating member, said spring strip carrying an operating member and having an extendable portion movable inwardly in a lateral direction transverse to said longitudinal axis of said penetrating member from an extended position to a retracted position during penetration of the anatomical cavity wall and outwardly in the lateral direction from said retracted position to said extended position upon introduction of said extendable portion in the anatomical cavity, said extendable portion of said spring strip being disposed outwardly of said cannula in said extended position; and a releasing mechanism including a mechanical trigger member operatively associated with said locking mechanism for triggering release of said locking mechanism in response to mechanical engagement of said operating member with said trigger member caused by lateral movement of said extendable portion from said retracted position to said extended position.

2. A safety penetrating instrument as recited in claim 1 wherein said extendable portion of said spring strip is adjacent said distal end of said cannula when said penetrating member is in said penetrating position.

3. A safety penetrating instrument as recited in claim 2 wherein said distal end of said cannula is slotted to receive said extendable portion of said spring strip when said penetrating member is in said penetrating position and said extendable portion is in said extended position.

4. A safety penetrating instrument as recited in claim 1 wherein said penetrating member is hollow and said extendable portion extends through an opening formed in said penetrating member adjacent said distal end of said penetrating member.

5. A safety penetrating instrument as recited in claim 4 wherein said spring strip is slidably disposed in said penetrating member and secured at one end to an inside surface of said penetrating member distal end.

6. A safety penetrating instrument as recited in claim 5 wherein said operating member is carried at a proximal end of said spring strip.

7. A safety penetrating instrument as recited in claim 6 wherein said locking mechanism includes a latch engaging said penetrating member and said trigger member includes a hook portion formed integrally with said latch in a manner to be axially aligned with said operating member of said spring strip.

8. A safety penetrating instrument as recited in claim 7 wherein said trigger member and latch are formed by a spring disposed in said penetrating member and wherein said latch extends through an opening in said penetrating member to engage structure within the penetrating instrument.

9. A safety penetrating instrument as recited in claim 8 and further comprising a hub mounting a proximal end of said penetrating member, wherein said latch extends through an opening in said penetrating member to engage structure within said hub.

10. A safety penetrating instrument as recited in claim 8 and further comprising a protective sheath disposed between said penetrating member and said cannula and a hub mounting a proximal end of said protective sheath, wherein said latch extends through an opening in said penetrating member to engage an opening in said protective sheath.

11. A safety penetrating instrument as recited in claim 9 and further comprising a guide tube disposed within said hub around said penetrating member, wherein said structure engaged by said latch includes an opening in said guide tube.

12. A safety penetrating instrument as recited in claim 7 wherein said operating member is a hook.

13. A safety penetrating instrument as recited in claim 7 and further comprising a hub mounting a proximal end of said penetrating member, wherein said locking mechanism includes a locking spring mounted in said hub externally of said penetrating member, said locking spring having a contracted position to fit within said penetrating member when said penetrating member is in said protected position and an expanded position to lock said penetrating member in said penetrating position.

14. A safety penetrating instrument as recited in claim 13 wherein said locking spring includes a pair of arms angled outwardly from opposite ends of a base portion, each arm carrying a latch at a distal end for engaging said penetrating member in said penetrating position.

15. A safety penetrating instrument as recited in claim 14 wherein said trigger member is formed by hook portions depending from each latch and said operating member includes a tapered portion axially aligned with said hook portions.

* * * * *